(12) United States Patent
Guo et al.

(10) Patent No.: US 12,385,004 B2
(45) Date of Patent: Aug. 12, 2025

(54) BACILLUS ARYABHATTAI HAVING FUNCTION OF HYDROLYZING SILICON AND USE THEREOF

(71) Applicant: HEBEI MONBAND WATER SOLUBLE FERTILIZER CO., LTD, Hebei (CN)

(72) Inventors: Yitao Guo, Hebei (CN); Xinglong Guo, Hebei (CN); Guangli Wu, Hebei (CN); Guoming Meng, Hebei (CN); Ying Yuan, Hebei (CN); Yaowei Kang, Hebei (CN)

(73) Assignee: Hebei Monband Water Soluble Fertilizer Co., Ltd, Hebei (CN)

( * ) Notice: Subject to any disclaimer, the term of this patent is extended or adjusted under 35 U.S.C. 154(b) by 1265 days.

(21) Appl. No.: 16/976,717

(22) PCT Filed: Apr. 27, 2020

(86) PCT No.: PCT/CN2020/087305
§ 371 (c)(1),
(2) Date: Aug. 28, 2020

(87) PCT Pub. No.: WO2020/177777
PCT Pub. Date: Sep. 10, 2020

(65) Prior Publication Data
US 2021/0002604 A1     Jan. 7, 2021

(30) Foreign Application Priority Data
Mar. 4, 2019    (CN) .......................... 201910161378.2

(51) Int. Cl.
| | |
|---|---|
| *C12N 1/20* | (2006.01) |
| *C05D 1/00* | (2006.01) |
| *C05D 9/00* | (2006.01) |
| *C05F 11/08* | (2006.01) |
| *C12R 1/07* | (2006.01) |

(52) U.S. Cl.
CPC ................ *C12N 1/20* (2013.01); *C05D 1/00* (2013.01); *C05D 9/00* (2013.01); *C05F 11/08* (2013.01); *C12N 1/205* (2021.05); *C12R 2001/07* (2021.05)

(58) Field of Classification Search
None
See application file for complete search history.

(56) References Cited

U.S. PATENT DOCUMENTS 10,555,532 B2    2/2020    Thompson et al.

FOREIGN PATENT DOCUMENTS

| | | |
|---|---|---|
| CA | 2907438 | 9/2014 |
| CN | 102212496 | 10/2011 |
| CN | 103045650 | 4/2013 |
| CN | 103952349 | 7/2014 |
| CN | 105408468 | 3/2016 |
| CN | 106244496 | 12/2016 |
| CN | 107189786 | 9/2017 |
| CN | 109706102 | 5/2019 |
| KR | 101733130 | 5/2017 |
| WO | 2019/035067 | 2/2019 |

OTHER PUBLICATIONS

Kizer et al. Appl Environ Microbiol. May 2008;74(10):3229-41 (Year: 2008).*
Prather et al. Curr Opin Biotechnol. Oct. 2008;19(5):468-74. (Year: 2008).*
International Search Report and Written Opinion corresponding to International Application No. PCT/CN2020/087305 mailed Aug. 3, 2020.
Office Action corresponding to Chinese Application No. 201910161378.2 issued Apr. 28, 2020.

* cited by examiner

*Primary Examiner* — Christian L Fronda
(74) *Attorney, Agent, or Firm* — Myers Bigel, P.A.

(57) ABSTRACT

The present disclosure relates to the field of microbiology, in particular to *Bacillus aryabhattai* having the function of hydrolyzing silicon and use thereof. The strain is selected from those: 1) preserved in China General Microbiological Culture Collection Center with the preservation number: CGMCC No. 17204; and preserved on Jan. 16, 2019; and/or 2) preserved in China General Microbiological Culture Collection Center with the preservation number: CGMCC No. 17203; and preserved on Jan. 16, 2019. The strain has the ability to hydrolyze silicon, and can also promote plant growth, and have alkali resistance, salt resistance and hypoxia resistance, thus having a very good application prospect.

4 Claims, 2 Drawing Sheets
Specification includes a Sequence Listing.

SEQUENCE LISTING

```
<160> NUMBER OF SEQ ID NOS: 2

<210> SEQ ID NO 1
<211> LENGTH: 1447
<212> TYPE: DNA
<213> ORGANISM: Bacillus Aryabhattai

<400> SEQUENCE: 1
actgtcactt agcggctagc tccttacggt tactccaccg acttcgggtg ttacaaactc      60
tcgtggtgtg acgggcggtg tgtacaaggc ccgggaacgt attcaccgcg gcatgctgat     120
ccgcgattac tagcgattcc agcttcatgt aggcgagttg cagcctacaa tccgaactga     180
```

```
gaatggtttt atgggattgg cttgacctcg cggtcttgca gccctttgta ccatccattg    240
tagcacgtgt gtagcccagg tcataagggg catgatgatt tgacgtcatc cccaccttcc    300
tccggtttgt caccggcagt caccttagag tgcccaactg aatgctggca actaagatca    360
agggttgcgc tcgttgcggg acttaaccca acatctcacg acacgagctg acgacaacca    420
tgcaccacct gtcactctgt ccccgaagg ggaacgctct atctctagag ttgtcagagg      480
atgtcaagac ctggtaaggt tcttcgcgtt gcttcgaatt aaaccacatg ctccaccgct    540
tgtgcgggcc cccgtcaatt cctttgagtt tcagtcttgc gaccgtactc cccaggcgga    600
gtgcttaatg cgttagctgc agcactaaag ggcggaaacc ctctaacact tagcactcat    660
cgtttacggc gtggactacc agggtatcta atcctgtttg ctccccacgc tttcgcgcct    720
cagcgtcagt tacagaccaa aaagccgctt tcgccactgg tgttcctcca catctctacg    780
catttcaccg ctacacgtgg aattccgctt ttctcttctg cactcaagtt ccccagtttc    840
caatgaccct ccacggttga gccgtgggct ttcacatcag acttaagaaa ccgcctgcgc    900
gcgctttacg cccaataatt ccggataacg cttgccacct acgtattacc gcggctgctg    960
gcacgtagtt agccgtggct ttctggttag gtaccgtcaa ggtacagcag ttactctcg    1020 tacttgttct tccctaacaa cagagtttta cgacccgaaa gccttcatca ctcacgcggc   1080
gttgctccgt cagactttcg tccattgcgg aagattccct actgctgcct cccgtaggag   1140
tctgggccgt gtctcagtcc cagtgtggcc gatcaccctc tcaggtcggc tatgcatcgt   1200
tgccttggtg agccgttacc tcaccaacta gctaatgcac gcgggccca tctgtaagtg    1260 atagccgaaa ccatctttca atcatctccc atgaaggaga agatcctatc cggtattagc   1320 ttcggttttcc cgaagttatc ccagtcttac aggcaggttg cccacgtgtt actcacccgt   1380
ccgccgctaa cgtcatagaa gcaagcttct aatcagttcg ctcgacttgc atgtatagca   1440
cgccgcc                                                             1447

<210> SEQ ID NO 2
<211> LENGTH: 1447
<212> TYPE: DNA
<213> ORGANISM: Bacillus Aryabhattai

<400> SEQUENCE: 2
cctgatcact tagcggctag ctccttacgg ttactccacc gacttcgggt gttacaaact     60
ctcgtggtgt gacgggcggt gtgtacaagg cccgggaacg tattcaccgc ggcatgctga    120
tccgcgatta ctagcgattc cagcttcatg taggcgagtt gcagcctaca atccgaactg    180
agaatggttt tatgggattg gcttgacctc gcggtcttgc agcccttgt accatccatt     240 gtagcacgtg tgtagcccag gtcataaggg gcatgatgat tgacgtcat ccccaccttc     300 ctccggtttg tcaccggcag tcaccttaga gtgcccaact aaatgctggc aactaagatc    360
aagggttgcg ctcgttgcgg gacttaaccc aacatctcac gacacgagct gacgacaacc    420
atgcaccacc tgtcactctg tccccgaag gggaacgctc tatctctaga gttgtcagag     480
gatgtcaaga cctggtaagg ttcttcgcgt tgcttcgaat taaaccacat gctccaccgc    540
ttgtgcgggc cccgtcaat tcctttgagt ttcagtcttg cgaccgtact cccaggcgg      600 agtgcttaat gcgttagctg cagcactaaa gggcggaaac cctctaacac ttagcactca    660
tcgtttacgg cgtggactac cagggtatct aatcctgttt gctccccacg ctttcgcgcc    720
tcagcgtcag ttacagacca aaaagccgcc ttcgccactg gtgttcctcc acatctctac    780
```

```
gcatttcacc gctacacgtg gaattccgct tttctcttct gcactcaagt tccccagttt    840
ccaatgaccc tccacggttg agccgtgggc tttcacatca gacttaagaa accgcctgcg    900
cgcgctttac gcccaataat tccggataac gcttgccacc tacgtattac cgcggctgct    960
ggcacgtagt tagccgtggc tttctggtta ggtaccgtca aggtacaagc agttactctt   1020
gtacttgttc ttccctaaca acagagtttt acgacccgaa agccttcatc actcacgcgg   1080
cgttgctccg tcagactttc gtccattgcg gaagattccc tactgctgcc tcccgtagga   1140
gtctgggccg tgtctcagtc ccagtgtggc cgatcaccct ctcaggtcgg ctatgcatcg   1200
ttgccttggt gagccgttac ctcaccaact agctaatgca ccgcgggccc atctgtaagt   1260
gatagccgaa accatctttc aatcatctcc catgaaggag aagatcctat ccggtattag   1320
cttcggtttc ccgaagttat cccagtctta caggcaggtt gcccacgtgt tactcacccg   1380
tccgccgcta acgtcataga agcaagcttc taatcagttc gctcgacttg catgtatagc   1440
acccgca                                                             1447
```

BACILLUS ARYABHATTAI HAVING FUNCTION OF HYDROLYZING SILICON AND USE THEREOF

CROSS-REFERENCE TO RELATED APPLICATION

The present application is a 35 U.S.C. § 371 national phase application of PCT Application No. PCT/CN2020/087305 filed on Apr. 27, 2020, which claims priority to Chinese Application No. 201910161378.2 filed on Mar. 4, 2019, the contents of each of which are incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled 1568-2_ST25.txt, 4,536 bytes in size, generated on Aug. 14, 2020 and filed via EFS-Web, is provided in lieu of a paper copy. This Sequence Listing is hereby incorporated by reference into the specification for its disclosures.

FIELD OF THE INVENTION

The present disclosure relates to the field of microbiology, in particular to *Bacillus aryabhattai* having the function of hydrolyzing silicon and use thereof.

BACKGROUND OF THE INVENTION

The silicon element has been confirmed by the international soil science community to be a fourth plant nutrient element after nitrogen, phosphorus and potassium elements, which is an essential nutrient for the growth of the grass family and root crops. Studies show that after silicon is applied to rice, the nitrogen content in the ears is increased, starch and protein synthesis is also promoted, and rice kernels are full; silicon has remarkable promoting effect on the absorption and accumulation of nitrogen element by wax gourd, and the content of nitrogen element and mineral elements during maturation is positively related to the amount of silicon applied; the application of silicon can improve the effectiveness of phosphorus in soil and the phosphorus content of plants, so that potassium in plants is greatly increased or slightly increased; meanwhile, the application of silicon fertilizer has obvious improvement effect on the growth, yield and quality of crops such as rice, oat, wheat, sugarcane, and sorghum. Besides the function in the aspect of plant growth, the silicon element can also improve the disease resistance and insect resistance of plants, relieve the poisoning of metal ions, relieve salt stress, and enhance drought resistance. Due to some predatory planting modes, the content of effective silicon in soil is greatly reduced, and the silicon-deficient farmland accounts for more than 50% of the area of the national farmland, therefore, using silicon fertilizer is of great practical significance.

Since silicon is distributed extremely widely in nature, next to oxygen, the content of silicon in the earth crust occupies the second position, mainly existing in forms of silica and silicates. The silicon content in soil is about 70%, but it is in a quite stable crystalline state and amorphous state, with very low solubility, which is hard to be absorbed by plants. Therefore, screening microorganisms that can decompose insoluble silicon-containing minerals in soil, and developing biological silicon fertilizers become important ways for solving the problems related to silicon fertilizers. The microbial fertilizer not only can effectively utilize the insoluble silicon-containing minerals in the soil, but also can meanwhile resist diseases and improve the soil, thereby achieving multiple purposes.

Domestically, silicon-hydrolyzing microorganisms are mostly silicate bacteria, for example, *Bacillus mucilaginosus*. They are a class of bacteria capable of freeing potassium from water-insoluble potassium minerals, and also called as potassium bacteria. The bacteria have been developed into microbial fertilizer for improving potassium fertilizer utilization. Some reports indicate that such bacteria have the function of hydrolyzing silicon. Besides, microorganisms such as *Pseudomonas, Rhizobium*, and spore bacteria are also reported abroad to have the function of hydrolyzing silicon, but these bacteria found are not very powerful for hydrolyzing silicate minerals, and there is no report that they are developed into silicon fertilizers converting silicon minerals to be absorbable and usable by plants.

In April 2009, Indian scientists found at the top of the Earth's isothermal layer three kinds of new microbial bacteria, which, not existing on the earth, have the ability to resist strong ultraviolet radiation. The scientists found 12 kinds of bacteria and 6 kinds of fungi in total in samples, wherein 8 kinds of microorganisms have 98% similarity to known microbial species on the earth based on the 16S rRNA gene sequence. However, three kinds of the bacteria therein are new species, and they have much higher anti-ultraviolet capability than their neighboring species. However, in current researches, scientists do not determine the origins of the 3 kinds of microorganisms from the isothermal layer, and in future researches, scientists will further explore to reveal the mystery of their origins. The first kind of new microbial bacterium is named "*Janibacter hoylei*" after the honored astrophysicist Fred Hoyle; the second kind of microbial bacterium is named "*Bacillus isronensis*", which name represents recognition of this balloon experiment successfully made by Indian Space Research Organization (ISRO); and the third kind of microbial bacterium is named "*Bacillus aryabhata*" (also called as *Bacillus aryabhattai*) after a famous ancient Indian astronomer Aryabhata.

In the prior art, it is reported that strains of *Bacillus aryabhattai* can degrade bagasse (single bacterium verification), so as to produce glucose and fructose; the colonies are circular and yellow, and have a smooth and orderly edge. But the relevant researches on *Bacillus aryabhattai* remain insufficiently intensive, especially there are quite few screenings and researches on *Bacillus aryabhattai* strains with specific functions.

SUMMARY

The present disclosure relates to an isolated *Bacillus aryabhattai* strain, which is selected from those:
1) preserved in China General Microbiological Culture Collection Center with the preservation number: CGMCC No. 17204; and preserved on Jan. 16, 2019; and/or
2) preserved in China General Microbiological Culture Collection Center with the preservation number: CGMCC No. 17203; and preserved on Jan. 16, 2019.

CGMCC No. 17203 and CGMCC No. 17204 are both preserved in China General Microbiological Culture Collection Center, with the address of No. 3, Yard No. 1, Beichen West Road, Chaoyang District, Beijing.

The present disclosure further claims to protect progenies, mutants or derivatives of the above strains.

According to another aspect of the present disclosure, the present disclosure further relates to a composition, which contains the strain as described above.

According to another aspect of the present disclosure, the present disclosure further relates to use of the strain as described above, or the composition as described above, in hydrolyzing silicon.

According to another aspect of the present disclosure, the present disclosure further relates to a method of enhancing health, growth or yield of plants, and the method includes application of an effective amount of the composition as described above to the plants or to surrounding environment of the plants.

The inventors surprisingly found that this strain has the ability to hydrolyze silicon, and further can promote plant growth, alkali resistance, salt resistance and hypoxia resistance, thus having a very good application prospect.

The *Bacillus aryabhattai* strain provided in the present disclosure is selected from:
1) an isolated *Bacillus aryabhattai* strain I, preserved in China General Microbiological Culture Collection Center, with the preservation number: CGMCC No. 17204; and preserved on Jan. 16, 2019;
2) an isolated *Bacillus aryabhattai* strain II, preserved in China General Microbiological Culture Collection Center, with the preservation number: CGMCC No. 17203; and preserved on Jan. 16, 2019;
3) progenies, mutants or derivatives of the isolated *Bacillus aryabhattai* strain I, wherein the progenies, mutants or derivatives of the isolated *Bacillus aryabhattai* strain I have the function of hydrolyzing silicon; and/or
4) progenies, mutants or derivatives of the isolated *Bacillus aryabhattai* strain II, wherein the progenies, mutants or derivatives of the isolated *Bacillus aryabhattai* strain II have the function of hydrolyzing silicon.

In one or more embodiments, the progenies, mutants or derivatives of the isolated *Bacillus aryabhattai* strain I and the progenies, mutants or derivatives of the isolated *Bacillus aryabhattai* strain II further have the function of promoting plant growth.

In one or more embodiments, the progenies, mutants or derivatives of the isolated *Bacillus aryabhattai* strain I and the progenies, mutants or derivatives of the isolated *Bacillus aryabhattai* strain II further have the function of increasing dry weight of crop roots.

In one or more embodiments, the progenies, mutants or derivatives of the isolated *Bacillus aryabhattai* strain I and the progenies, mutants or derivatives of the isolated *Bacillus aryabhattai* strain II still have the function of hydrolyzing silicon in a cultivation system containing no more than 5% NaCl.

In one or more embodiments, the progenies, mutants or derivatives of the isolated *Bacillus aryabhattai* strain I and the progenies, mutants or derivatives of the isolated *Bacillus aryabhattai* strain II still can grow in a cultivation system containing no more than 20% $KNO_3$, and still have the function of hydrolyzing silicon in a cultivation system containing no more than 10% $KNO_3$.

In one or more embodiments, the progenies, mutants or derivatives of the isolated *Bacillus aryabhattai* strain I and the progenies, mutants or derivatives of the isolated *Bacillus aryabhattai* strain II still have the function of hydrolyzing silicon in a cultivation system of $6.5 \leq pH \leq 10$.

In one or more embodiments, the progenies, mutants or derivatives of the isolated *Bacillus aryabhattai* strain I and the progenies, mutants or derivatives of the isolated *Bacillus aryabhattai* strain II still have the function of hydrolyzing silicon in a cultivation system with an oxygen concentration no less than 10%.

In one or more embodiments, 16S rRNA sequences of the progenies, mutants or derivatives of the isolated *Bacillus aryabhattai* strain I have at least 99% homology with 16S rRNA sequence of the isolated *Bacillus aryabhattai* strain I.

In one or more embodiments, 16S rRNA sequences of the progenies, mutants or derivatives of the isolated *Bacillus aryabhattai* strain II have at least 99% homology with 16S rRNA sequence of the isolated *Bacillus aryabhattai* strain II.

Genomic sequences have at least 90% identity to the genomic sequence of the isolated *Bacillus aryabhattai* strain I.

In one or more embodiments, genomic sequences of the progenies, mutants or derivatives of the isolated *Bacillus aryabhattai* strain II have at least 90% identity to a genomic sequence of the isolated *Bacillus aryabhattai* strain II.

The present disclosure provides a composition, which contains a culture of the isolated *Bacillus aryabhattai* strain I, the isolated *Bacillus aryabhattai* strain II, the progenies, mutants or derivatives of the isolated *Bacillus aryabhattai* strain I and/or the progenies, mutants or derivatives of the isolated *Bacillus aryabhattai* strain II, defined in the present disclosure.

In one or more embodiments, the composition is in the form of liquid, frozen or dried powder.

In one or more embodiments, the composition further contains an agriculturally effective amount of compound or composition selected from the group consisting of nutrients, fertilizers, acaricides, bactericides, fungicides, insecticides, microbicides, nematicides and pesticides.

In one or more embodiments, the composition further contains a silicon fertilizer, and the silicon fertilizer contains elemental silicon, an organosilicon compound and/or an inorganic silicon compound.

In one or more embodiments, the composition further contains a potassium fertilizer, and the potassium fertilizer contains elemental potassium, an organic potassium compound and/or an inorganic potassium compound.

The present disclosure provides use of the *Bacillus aryabhattai* strain or the composition described herein in hydrolyzing silicon.

In one or more embodiments, the silicon is present in the form of elemental silicon or silicon ion.

In one or more embodiments, the silicon is present in the form of an associate of silicon ion with another element or a bonding compound of silicon ion complexed with another element.

In one or more embodiments, the silicon is present in the form of silicate or silicon-containing mineral.

In one or more embodiments, the silicon is present in the form of silicate.

In one or more embodiments, the silicate is selected from the group consisting of magnesium silicate, magnesium fluorosilicate, magnesium aluminum silicate, sodium silicate, potassium silicate and sodium potassium silicate.

In one or more embodiments, the silicon is present in the form of silicon-containing mineral.

In one or more embodiments, the silicon-containing mineral is selected from the group consisting of nesosilicate minerals, disilicate minerals, cyclic silicate minerals, chain silicate minerals, single-chain silicates, double-chain silicates, phyllosilicate minerals and tectosilicate minerals.

In one or more embodiments, the silicon is present in the form of pyroxenes, olivines, epidotes, tourmalines, hornblendes, mica, carclazyte, feldspar or quartz.

The present disclosure provides a method of enhancing health, growth or yield of plants, and the method includes application of an effective amount of the composition described herein to the plants or to surrounding environment of the plants.

In one or more embodiments, the enhancing health, growth or yield of plants includes promoting growth of roots of the plants.

In one or more embodiments, the plants include wheat, rice, corn, baby cabbage, tomato, cucumber, broccoli, strawberry and/or grape.

BRIEF DESCRIPTION OF DRAWINGS

In order to more clearly illustrate the technical solutions in specific embodiments of the present disclosure or in the prior art, drawings which need to be used for description of the specific embodiments or the prior art will be introduced briefly below, and apparently, the drawings in the description below merely show some embodiments of the present disclosure, and a person ordinarily skilled in the art still could obtain other drawings in light of these drawings without inventive efforts.

*Bacillus aryabhattai* provided in the present disclosure:
1) the name of a strain is MB35-5, with preservation number of CGMCC No. 17204; and
2) the name of a strain is MB22, with preservation number of CGMCC No. 17203.

Both of them are preserved in China General Microbiological Culture Collection Center; and upon detection by the preservation center on Jan. 16, 2019, they are live strains and preserved.

DETAILED DESCRIPTION OF EMBODIMENTS

In order to make the objects, technical solutions and advantages of the embodiments of the present disclosure clearer, the technical solutions in the embodiments of the present disclosure will be described below clearly and completely. If no specific conditions are specified in the embodiments, they are carried out under normal conditions or conditions recommended by the manufacturer. If the manufacturers of reagents or apparatus used are not specified, they are all conventional products commercially available.

Unless otherwise defined herein, scientific and technical terms used in the present disclosure should have meanings that are commonly understood by those ordinarily skilled in the art. Exemplary methods and materials are described below, but methods and materials similar or equivalent to those described herein can also be used in the practice or testing of the present disclosure.

The present disclosure relates to an isolated *Bacillus aryabhattai* strain, which is selected from those:

1) preserved in China General Microbiological Culture Collection Center with the preservation number: CGMCC No. 17204; and preserved on Jan. 16, 2019; and/or
2) preserved in China General Microbiological Culture Collection Center with the preservation number: CGMCC No. 17203; and preserved on Jan. 16, 2019.

The above strains have the function of hydrolyzing silicon.

The function of hydrolyzing silicon can be determined according to the method defined in the part "3 Determination of Ability to Hydrolyze Silicon" in the examples of the present disclosure, wherein circles formed by hydrolysis of silicon by the MB35-5 strain are sized about 4.5 mm, for example, 6 mm, 5 mm, 4 mm, 3.5 mm, 3 mm, 2.5 mm, or 2 mm; and circles formed by hydrolysis of silicon by the MB22 strain are sized about 6 mm, for example, 8 mm, 7 mm, 6.5 mm, 6 mm, 3 mm, 2.5 mm, or 2 mm.

According to one aspect of the present disclosure, the present disclosure further relates to a *Bacillus aryabhattai* strain having following characteristics:
a) it is a progeny, mutant or derivative of the above strains, and
b) it has the function of hydrolyzing silicon.

The present disclosure claims to protect the *Bacillus aryabhattai* strains having the above preservation numbers, and strains of progenies, mutants and derivatives that are mutated within a suitable range but still have quite strong ability to hydrolyze silicon.

As used herein, the term "strains of progenies, mutants and derivatives of *Bacillus aryabhattai* strain" refers to *Bacillus aryabhattai* strains whose genome is highly similar to that of the MB35-5 or MB22 strain. In the present disclosure, a mutant strain can be defined in such a manner that the mutant strain has 99% or higher homology (e.g., 99.1%, 99.2%, 99.3%, 99.4%, 99.5%, 99.6%, 99.7%, 99.8%, 99.9% homology) to 16S rRNA represented by SEQ ID NO. 1 (MB35-5) or SEQ ID NO. 2 (MB22). In one or more embodiments, the "strains of progenies, mutants and derivatives of *Bacillus aryabhattai* strain" have at least 99%, at least 99.1%, at least 99.2%, at least 99.3%, at least 99.4%, at least 99.5%, at least 99.6%, at least 99.7%, at least 99.8% or at least 99.9% homology with the 16S rRNA of the MB35-5 or MB22 strain.

The term "strains of progenies, mutants and derivatives of *Bacillus aryabhattai* strain" or mutant strain also may be covered by way of being highly similar in terms of genome. Compared with the genome of the MB35-5 or MB22 strain, the genome of a *Bacillus aryabhattai* strain contains at most 150 mutational events, for example, containing at most 140, 130, 120, 110, 100, 90, 80, 70, 60, 50, 40, 30 or 20 mutational events. Mutational events are defined as SNPs (single nucleotide polymorphisms) or INDELs (insertions, deletions, and combinations of both). The number of mutational events is determined as follows: the genome of the MB35-5 strain is used as a control to identify the mutational events present in the genome of a mutant strain, each type of mutational event (SNP or INDEL) representing one mutational event (i.e., for example, insertion of a sequence containing several nucleotides is only considered as one mutational event). In this context, the genomic sequence of a mutant strain in the present disclosure is defined by the number of mutational events contained compared with the MB35-5 or MB22 strain. Apart from the manner of defining the genomic sequence with the number of mutational events, the genomic sequence further can be additionally defined by the percentage of identity to the genomic sequence of the MB35-5 or MB22 strain, wherein the percentage of identity herein represents the percentage of sequences in the genome of one strain found to be present in the genome of another strain, specifically: a) the percentage of sequences found in the genome of the MB35-5 or MB22 strain and present in the genome of the mutant strain, or b) the percentage of sequences found in the genomic sequence of the mutant strain and present in the genome of the MB35-5 or MB22 strain. Thus, the mutant strains differing from the MB35-5 or MB22 strain only in insertion (one or more insertions) or only in deletion (one or more deletions) have a genome with a percentage of 100% identity to the genome of the MB35-5 or MB22 strain, because in the genome of a strain the entire genomic sequence of another strain is completely found. In one specific embodiment, the genomic sequence of the mutant strain of the present disclosure defined by the number of mutational events has at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, at least 99.9%, at least 99.92%, at least 99.94%, at least 99.96%, at least 99.98% or at least 99.99% identity to the genomic sequence of the MB35-5 or MB22 strain, wherein the percentage of identity represents the percentage of sequences found in the genome of one kind of strain and present in the genome of another kind of strain; identity is described in terms of comparing two genomic sequences over their full lengths (global alignment), and can be calculated using any program based on the Needleman-Wunsch algorithm.

CGMCC No. 17204 and/or CGMCC No. 17203 strain, and strains of progenies, mutants or derivatives thereof further have the function of promoting plant growth, for example, promoting growth of plant roots and increasing dry weight of crop roots.

CGMCC No. 17204 and/or CGMCC No. 17203 strain, and strains of progenies, mutants or derivatives thereof still have the function of hydrolyzing silicon in the cultivation system containing no more than 5% NaCl;

In one or more embodiments, the concentration may be selected to be, for example, 4.5% NaCl, 4% NaCl, 3.5% NaCl, 3% NaCl, or 2.5% NaCl.

In one or more embodiments, the concentration may be selected to be, for example, not higher than 4.5% NaCl, not higher than 4% NaCl, not higher than 3.5% NaCl, not higher than 3% NaCl, or not higher than 2.5% NaCl.

CGMCC No. 17204 and/or CGMCC No. 17203 strain still can grow in a cultivation system containing no more than 20% $KNO_3$, and still has the function of hydrolyzing silicon in a cultivation system containing no more than 10% $KNO_3$.

In one or more embodiments, the $KNO_3$ concentration in the growth system may be selected to be, for example, 19% $KNO_3$, 18% $KNO_3$, 17% $KNO_3$, 16% $KNO_3$, 15% $KNO_3$, 14% $KNO_3$, 13% $KNO_3$, 12% $KNO_3$, 11% $KNO_3$, 10% $KNO_3$, 9% $KNO_3$, 8% $KNO_3$, 7% $KNO_3$, 6% $KNO_3$, 5% $KNO_3$, 4% $KNO_3$, 3% $KNO_3$, or 2% $KNO_3$.

In one or more embodiments, the $KNO_3$ concentration in the growth system may be selected to be, for example, not higher than 19% $KNO_3$, not higher than 18% $KNO_3$, not higher than 17% $KNO_3$, not higher than 16% $KNO_3$, not higher than 15% $KNO_3$, not higher than 14% $KNO_3$, not higher than 13% $KNO_3$, not higher than 12% $KNO_3$, not higher than 11% $KNO_3$, not higher than 10% $KNO_3$, not higher than 9% $KNO_3$, not higher than 8% $KNO_3$, not higher than 7% $KNO_3$, not higher than 6% $KNO_3$, not higher than 5% $KNO_3$, not higher than 4% $KNO_3$, not higher than 3% $KNO_3$, or not higher than 2% $KNO_3$.

In one or more embodiments, the $KNO_3$ concentration in the silicon hydrolyzing system may be selected to be, for example, 9% $KNO_3$, 8% $KNO_3$, 7% $KNO_3$, 6% $KNO_3$, 5% $KNO_3$, 4% $KNO_3$, 3% $KNO_3$, or 2% $KNO_3$.

In one or more embodiments, the $KNO_3$ concentration in the silicon hydrolyzing system may be selected to be, for example, not higher than 9% $KNO_3$, not higher than 8% $KNO_3$, not higher than 7% $KNO_3$, not higher than 6% $KNO_3$, not higher than 5% $KNO_3$, not higher than 4% $KNO_3$, not higher than 3% $KNO_3$, or not higher than 2% $KNO_3$.

CGMCC No. 17204 and/or CGMCC No. 17203 strain, and strains of progenies, mutants and derivatives thereof still have the function of hydrolyzing silicon in the cultivation system of 6.5≤pH≤0; and pH may be selected to be 5, 6, 6.5, 7, 8, 9, or 10.

CGMCC No. 17204 and/or CGMCC No. 17203 strain, and strains of progenies, mutants and derivatives thereof still have the function of hydrolyzing silicon in the cultivation system containing no less than 10% oxygen concentration;

In one or more embodiments, the oxygen concentration also may be selected to be 15%, 20%, 25% or higher.

In one or more embodiments, the oxygen concentration also may be selected to be not less than 15%, not less than 20%, not less than 25% or more.

The present disclosure further relates to a composition, which contains a culture of the strain as described above.

In practical application process, considering possible need of transportation and other reasons, it is necessary to cultivate the *Bacillus aryabhattai* strain in large scale to prepare it into a form of composition (in particular, microbial agent), so as to expand the application range thereof.

The composition of the present disclosure (for example, when used as a starter culture) includes, but is not limited to, pure culture or mixed culture. Therefore, the present disclosure defines the pure culture as such a culture in which the whole or substantially the whole culture consists of the same kind of *Bacillus aryabhattai* strain of the present disclosure. In an alternative form, the mixed culture is defined as such a culture that contains several kinds of microorganisms, in particular containing several kinds of bacterial strains, including the *Bacillus aryabhattai* strain of the present disclosure and/or strains of progenies, mutants and derivatives thereof.

In some embodiments, the composition further includes a strain having a function of hydrolyzing potassium.

The composition is used in agriculture, and can be made into the form of liquid, frozen or dried powder; or into the form of preparations commonly used in the present industry, e.g., granule, suspension, wettable powder, emulsion or liquid formulation.

Any carriers may be used, no matter they are solid or liquid, as long as they are commonly used for agricultural and horticultural pesticides and biologically inert. No particular carrier is limited.

In some specific embodiments, when being in the form of frozen or dried powder, the composition includes a solid carrier;

Examples of solid carrier include mineral powders, such as china clay, talc, bentonite, zeolite, calcium carbonate, diatomaceous earth and white carbon; vegetable flours, such as corn flour and starch; and high molecular compounds, such as polyalkylene glycols, for example, polyvinyl alcohol. On the other hand, typical liquid carriers include various organic solvents, such as decane and dodecane, vegetable oils, mineral oils and water.

In some embodiments, the solid carrier includes one or more of peat, turf, talc, lignite, pyrophillite, montmorillonite, alginate, filter-pressing slurry, sawdust, perlite, mica, silica, quartz powder, calcium-based bentonite, vermiculite, kaolin, light calcium carbonate, diatomaceous earth, maifanite, calcite, zeolite, white carbon black, fine sand and clay.

In some embodiments, the composition contains an adjuvant. For example, the composition includes, but is not limited to, surfactants, binders, stabilizers and the like, which are commonly used as adjuvants in agricultural and horticultural chemicals, either used alone or used in combination as needed, and/or stabilizers, such as antioxidants and/or pH regulators. Light stabilizers may also be used in some cases.

A total content of these adjuvants may be 0 wt % to 80 wt %, and a content of the carrier is a value obtained by subtracting the contents of active ingredients and adjuvants from 100 wt %.

In some specific embodiments, the adjuvant includes one or more selected from the group consisting of sodium dodecyl benzene sulfonate, sodium butylnaphthalene sulfonate, trehalose, glycerol, sodium lignosulfonate, sodium alkylnaphthalene sultanate polycondensates, niacin, alcohol, buffer salts, sodium chloride, amino acids, vitamins, proteins, polypeptides, polysaccharides or monosaccharides, yeast extract, white carbon black, tea saponin, and skim milk.

In some specific embodiments, the composition further contains an agriculturally effective amount of compound or composition selected from the group consisting of nutrients, fertilizers, acaricides, bactericides, fungicides, insecticides, microbicides, nematicides and pesticides. For example, the composition further contains a fertilizer, for example, silicon fertilizer and potassium fertilizer. The silicon fertilizer is in the form of elemental silicon, organosilicon compound and/or inorganic silicon compound. The potassium fertilizer is in the form of elemental potassium, organic potassium compound and/or inorganic potassium compound.

The above-mentioned ingredients may be combined with the strains provided in the present disclosure, so as to achieve better technical effects.

In some embodiments, in the composition, the number of viable bacteria of the *Bacillus aryabhattai* strain is $10^{7-12}$ cfu·mL$^{-1}$ or $10^{7-12}$ cfu·g$^{-1}$.

$10^8$ cfu·mL$^{-1}$, $10^9$ cfu·mL$^{-1}$, $10^{10}$ cfu·mL$^{-1}$, $10^{11}$ cfu·mL$^{-1}$ or $10^8$ cfu·g$^{-1}$, $10^9$ cfu·g$^{-1}$, $10^{10}$ cfu·g$^{-1}$, $10^{11}$ cfu·g$^{-1}$ also may be selected.

The present disclosure further relates to use of the strain as described above, or the composition as described above, in hydrolyzing silicon.

In some embodiments, the silicon is present in the form of elemental silicon or silicon ion.

In some embodiments, the silicon is present in the form of an associate of silicon ion with another element or a bonding compound of silicon ion complexed with another element.

In some embodiments, the silicon is present in the form of silicate or silicon-containing mineral.

In one or more embodiments, the silicate may be selected from the group consisting of magnesium silicate, magnesium fluorosilicate, magnesium aluminum silicate, sodium silicate, potassium silicate or sodium potassium silicate and so on.

In one or more embodiments, the silicon-containing mineral may be selected from the group consisting of nesosilicate minerals, disilicate minerals, cyclic silicate minerals, chain silicate minerals, single-chain silicates, double-chain silicates, phyllosilicate minerals, and tectosilicate minerals;

In one or more embodiments, common silicon forms are, for example, pyroxenes, olivines, epidotes, tourmalines, hornblendes, mica, carclazyte, feldspar or quartz.

The present disclosure further relates to a method of enhancing health, growth or yield of plants, and the method includes application of an effective amount of the composition as described above to the plants or to surrounding environment of the plants.

Embodiments of the present disclosure will be described in detail below in combination with examples, while a person skilled in the art would understand that the following examples are merely used for illustrating the present disclosure, but should not be considered as limitation on the scope of the present disclosure. If no specific conditions are specified in the examples, they are carried out under normal conditions or conditions recommended by manufacturers. If manufacturers of reagents or apparatuses used are not specified, they are all conventional products commercially available.

Examples

Experiment Steps

1 Bacterium Screening
1.1 Acquisition of Soil Samples

Representative soil such as sandy soil, clay and black soil was selected as sampling sites. Samples may derive from different regions such as farmland, pasture, forest, etc. Particularly, rice fields, wheat fields and soil using silicon fertilizers for many years were sampled, 15-20 grams of sample was acquired from each site, meanwhile the origin (province, county), acquisition year and month, the source of soil (plants, sandy soil, or others) of the samples acquired were labeled. The samples were stored in 80% glycerol tubes and preserved in −80° C. refrigerator.

1.2 Enrichment of Target Microorganisms in Soil Samples

First step enrichment: 1 g of soil sample was taken in 10 mL of purified water and shaken up to obtain a mixed liquid, 100 μL of the mixed liquid was taken and underwent shake culture in nutrient-deficient R2A liquid medium (yeast powder 0.5 g, tryptone 0.5 g, glucose 0.5 g, dipotassium hydrogen phosphate 0.3 g, sodium pyruvate 0.3 g, magnesium silicate 5.0 g, and water 1 L) at 30° C. for 3 days to obtain a cultured bacterial solution. The cultured bacterial solution was diluted $10^{-6}$, $10^{-7}$ and $10^{-8}$ times and then applied to R2A solid medium (yeast powder 0.5 g, tryptone 0.5 g, peptone 0.75 g, glucose 0.5 g, soluble starch 0.5 g, dipotassium hydrogen phosphate 0.3 g, sodium pyruvate 0.3 g, magnesium silicate 2.5 g, agar 15 g, and water 1 L), and functional strains were picked.

Second step enrichment: 100 μL of the bacterial solution prepared with the strain obtained in the previous step was taken, and underwent shake culture in ½N nutrient-deficient R2A medium (yeast powder 0.25 g, tryptone 0.25 g, glucose 0.5 g, dipotassium hydrogen phosphate 0.3 g, sodium pyruvate 0.3 g, magnesium silicate 5.0 g, and water 1 L) at 30° C. for 3 days to obtain a cultured bacterial solution. The cultured bacterial solution obtained was diluted $10^{-6}$, $10^{-7}$ and $10^{-8}$ times and then coated a vessel, and functional strains having circles formed by hydrolysis of silicon were picked.

Third step enrichment: 100 μL of the bacterial solution prepared with the strain obtained in the second step was taken, and underwent shake culture in ½N nutrient-deficient R2A medium at 30° C. for 3 days to obtain a cultured bacterial solution. The cultured bacterial solution obtained was diluted $10^{-6}$, $10^{-7}$, and $10^{-8}$ times and then coated a vessel, and functional strains having circles formed by hydrolysis of silicon were picked.

1.3 Repeated Verification

In order to ensure the sustainability of the strains' ability to hydrolyze silicon, the strains picked from an enrichment plate were inoculated in R2A solid medium containing 0.25% magnesium silicate, and cultured at 30° C. Experimental results were observed every day to verify whether the picked colonies had the function of hydrolyzing silicon, and exclude false positive colonies.

2 Bacterium Identification 2.1 Extracting Bacterial DNA by a CTAB Method

1) A single colony was inoculated in 5 ml of R2A medium, and cultured overnight at 30° C. to obtain a seed culture solution;
2) 1 ml of the seed culture solution was inoculated into 100 ml of R2A liquid medium, and cultured at 37° C. and 220 r/min for 16 hours to obtain a culture;
3) the culture was centrifuged at 5000 r/min for 10 minutes, and the supernatant was discarded to obtain thalli, After centrifuging and washing the thalli with 10 ml of TE, the thalli were suspended in 10 ml of TE to obtain a suspension, and the suspension was fully mixed, and stored at −20° C. for later use;
4) 3.5 ml of the bacterial suspension was taken, 10% SDS 184 μl was added and fully mixed, and 10 mg/ml protease K 37 μl was added and fully mixed, followed by incubation at 37° C. for 1 hour;
5) 5 mol/L NaCl 740 μl was added, and then CTAB/NaCl 512 μl was added and fully mixed, followed by incubation at 65° C. for 10 minutes;
6) an equal volume of chloroform/isoamyl alcohol was added and fully mixed, followed by centrifugation at 10000 r/min for 5 minutes, and the supernatant was retained;
7) an equal volume of phenol:chloroform:isoamyl alcohol (25:24:1) was added to the supernatant and fully mixed, followed by centrifugation at 10000 r/min for 5 minutes, and the supernatant was retained;
8) 0.6 times of isoamyl alcohol was added to the supernatant and fully mixed, followed by centrifugation at 10000 r/min for 5 minutes, DNA precipitate was collected, and the DNA precipitate was centrifuged and washed with 70% ethanol; and
9) the DNA precipitate was dissolved with 1 ml of TE, RNase A with a final concentration of 20 μg/ml was added, and the resultant was stored at 4° C.

2.2 Amplification and Sequencing

The extracted DNA was used as a template, and 16S rDNA universal primers 27f (5'-AGAGTTTGATCCTGGCTCAG-3') and 1492r (5'-GGTTACCTTGTTACGACTT-3') were adopted to carry out PCR amplification of 16S rDNA. PCR reaction condition included: pre-denaturation at 94° C. for 30 s; denaturation at 94° C. for 30 s; annealing at 52° C. for 30 s, extension at 72° C. for 60 s, 35 cycles. PCR product underwent 1.5% agarose gel electrophoresis. Having undergone the agarose gel electrophoresis, the PCR product was recovered, purified and sequenced (Beijing Meiyimei Biotechnology Co., Ltd). Homologous sequences were searched by Blast in GenBank according to the obtained 16S rDNA sequence, and phylogeny was established by MEGA5.0 software.

3 Determination of Ability to Hydrolyze Silicon

The strains obtained from screening in the previous step were inoculated in R2A medium containing 0.5% magnesium silicate. Silicate bacteria were used as positive control. After 48 h of inoculation, the colonies were rinsed, and the diameter of circles formed by hydrolysis of silicon on the medium was measured in unit of mm.

Ability to Hydrolyze Silicon=Diameter (mm) of Circle Formed by Hydrolysis of Silicon+$X$;

In the above, $X$ is a weighting coefficient, and is correspondingly −2, −1, 0, 1 or 2 according to the degree of transparency of circles formed by hydrolysis of silicon by the strains.

4 Observation of Strain Morphology

The screened strains were inoculated onto an R2A plate and cultured at 30° C. for 24 h, to observe colonies' size, shape, color, glossiness, viscosity, raised shape, transparency, edge characteristic and presence and absence of spore, and the like.

5 Determination of Stress Resistance of Strain

The screened strains were inoculated on R2A media under the conditions of pH 5, pH 10, 5% NaCl, 5% $KNO_3$, 10% $KNO_3$, and 20% $KNO_3$, and whether the strains grew or not, and whether the growth was inhibited and whether the growth rate was fast or slow were observed. Meanwhile, the strains' ability to hydrolyze silicon on the R2A (containing 1.0% magnesium silicate) media under the conditions of pH 5, pH 10, 5% NaCl, 10% NaCl, 5% $KNO_3$, 10% $KNO_3$ was further determined, and calculated according to the formula in 3.

6 Determination of Aerobism of Strain

Carbon dioxide and microaerobic Anaeropack manufactured by Mitsubishi Gas Chemical Company, INC were used to control the oxygen concentration at 15% and 10%, to verify the growth situation and ability to hydrolyze silicon of the strains under anoxic condition.

7 Hemolysis Detection

The strains obtained from the above screening were inoculated onto blood agar plate medium (10.0 g of casein pancreatin digest, 3.0 g of cardiac pancreatin digest, 1.0 g of corn starch, 13.0 g of agar, 5.0 g of meat pepsin digest, 5.0 g of yeast leaching powder, 5.0 g of sodium chloride, 1000 mL of distilled water, 60 mL of goat blood), and incubated in an incubator at 30° C. for 18 h. The morphology of colonies was observed, and whether hemolysis rings appeared was observed.

8 Determination of Sporulation Rate

Under the condition of sterile operation, a clean glass slide was first fired and sterilized with alcohol, and marked an obvious specimen area, a small drop of phosphate buffer solution (0.2 M, pH 7.2) was dropped in the area, 2-3 colonies were scraped using an inoculation loop, a small drop of bacterial suspension was dropped in the dropped phosphate buffer solution and applied uniformly to form a thin film, which was aired and fixed. After airing, 7.6% of malachite green solution was dropped on the biofilm, and fully covered the coated biofilm area, followed by dying for 15-20 minutes, and decoloration through washing with water until outflow water had no green color, the surface water was leached away, after airing, the biofilm was dyed again, and dropped with 0.5% of safranin solution, wherein the dying lasted for 2-3 minutes, the dye solution was poured out and slightly rinsed with water, and residual dye solution was sucked with filter paper, then the biofilm was aired, i.e.

the spore colony specimen was prepared. After drying, observation was made using an oil immersion lens, wherein the spore was green, and the sporangium and the trophosome were red.

At least three fields of view were observed, the number of spores and the number of bacteria in each field of view were counted, the average value of the number of spores (A) and the average value of the number of bacteria (B) were recorded and calculated, and the sporulation rate in the microscopic examination was calculated according to the following formula.

Sporulation Rate in Microscopic Examination: $N=A/(A+B)\times100\%$

In the formula: N represents the sporulation rate of the sample in microscopic examination;
A represents mean value of the number of spores in the field of view of microscopic examination of the sample; and
B represents mean value of the number of bacteria in the field of view of microscopic examination of the sample.

9 Potting Test

Taking vermiculite as matrix, each pot was filled with 500 g of soil, and each pot was moistened with an equivalent, small amount of water. Uniformly sized Zhengdan 958 and popcorn (Lvbao Seed Co., Ltd., Taigu County) seeds were chosen, and 6 seeds were planted per pot, with 4 pots of repetition. After the bacterial solution was diluted 50 times, an equal amount of the bacterial solution was used for irrigation in appropriate time and in an appropriate amount according to growth requirements of corn. The dry weight of roots was weighed after 15 days. A nutrient-deficient R2A liquid medium to which no strain was inoculated was used as blank control CK1, and a medium to which silicate bacteria were inoculated was used as positive control CK2.

Experiment Results

1 Strain Screening

In the present test, 34 soil samples of 19 crops, including wheat, rice, maize, baby cabbage, tomato, cucumber, broccoli, strawberry, grape and so on were collected in total from 16 cities and counties of 10 provinces. 206 strains having the function of hydrolyzing silicon were obtained through screening by enrichment experiment. Through 16S rDNA sequencing and verification of the ability of hydrolyzing silicon, stress resistance, aerobism, hemolysis, strain growth characteristics, sporulation rate and potting test, two Gram-positive strains-MB22 and MB35-5-having biosafety, high sporulation rate, strong ability to hydrolyze silicon, salt and alkali resistance, good growth under poor oxygen conditions, no hemolysis loop and promoting effect on plant growth, were selected therefrom. Through analysis of 16S rDNA sequences of the two strains, results indicate that they have up to 99% homology with *Bacillus aryabhattai*.

2 Strain Morphology

After growing on the R2A medium for 2 days, the colony was in a round shape, beige and opaque, smooth and relatively wet in surface, with a regular edge, halo, and central bulge, and had a diameter of 1.5-2 mm, and the colony was round, shiny, viscous, and slightly raised, and had a smooth and orderly edge.

3 Ability to Hydrolyze Silicon

Figure 1:
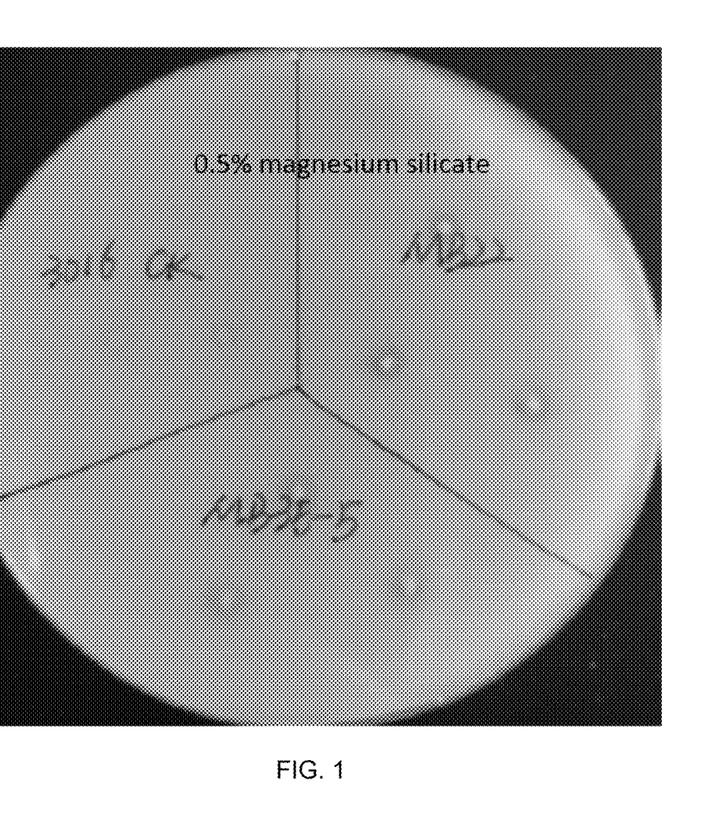
FIG. 1 shows determination results of abilities to hydrolyze silicon of strain MB22 and strain MB35-5 in one embodiment of the present disclosure.

Results in Table 1 and FIG. 1 indicate that strains MB22 and MB35-5 have significantly higher ability to hydrolyze silicon than the control silicate strain 3016.

TABLE 1

Strains' Ability to Hydrolyze Silicon on 0.5% Magnesium Silicate R2A Medium

| Strain | 3016 (CK) | MB35-5 | MB22 |
|---|---|---|---|
| Ability to Hydrolyze Silicon | 2 | 4.5 | 6 |

Figure 2:
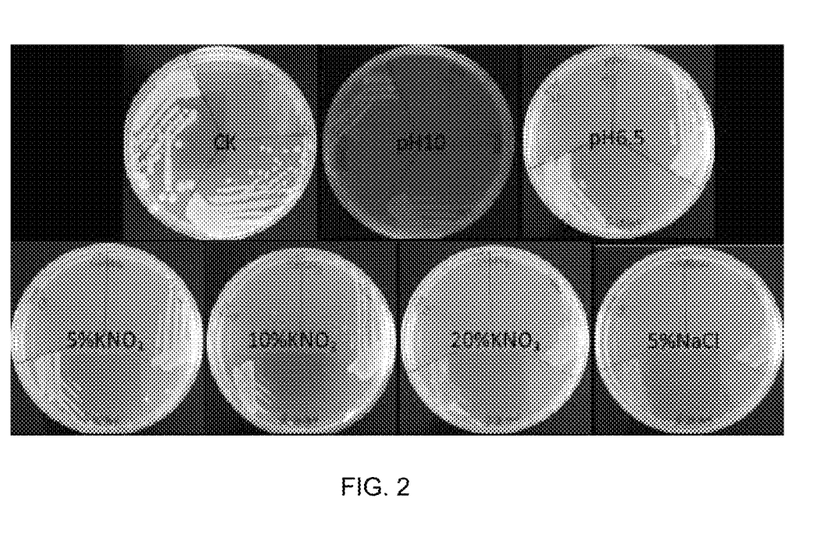
FIG. 2 shows determination results of salt resistance, and acid and alkali resistance of strains provided in one embodiment of the present disclosure.
Figure 3:
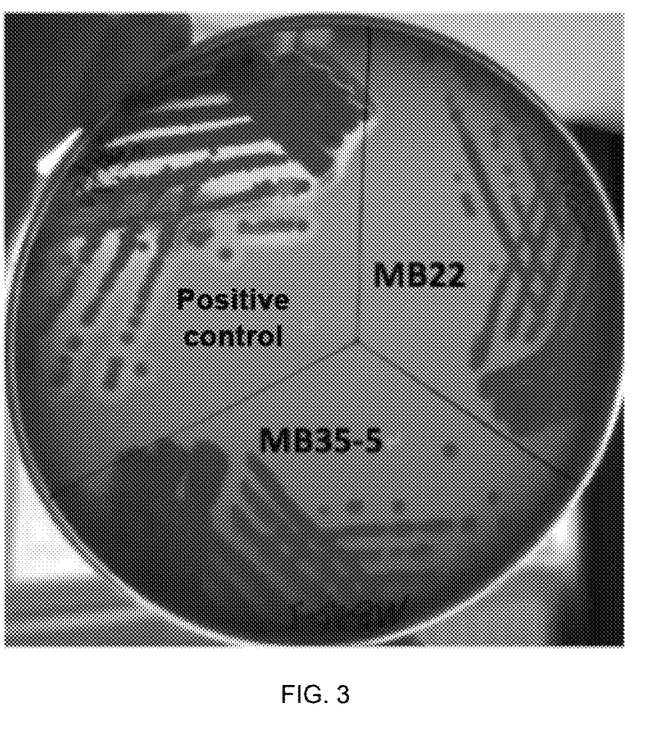
FIG. 3 shows the abilities to hydrolyze silicon of strains provided in one embodiment of the present disclosure under different culture conditions.

4 Stress Resistance of Strains: as indicated by the determination results in Table 2 and FIG. 2, the strains MB22 and MB35-5 of the present disclosure have better salt and alkali resistance properties compared with control strain 3016, and has certain acid resistance.

TABLE 2

Growth Situations of Strains under Different Conditions

| Strain | pH 5 | pH 6.5 | pH 7.0 | pH 10 | 5% NaCl | 5% KNO$_3$ | 10% KNO$_3$ | 20% KNO$_3$ |
|---|---|---|---|---|---|---|---|---|
| 3016 (CK) | − | − | + | − | − | − | − | − |
| MB22 | − | + | + | + | + | + | + | + |
| MB35-5 | − | + | + | + | + | + | + | + |

5 Ability to Hydrolyze Silicon in Adversity

The determination results (Table 3) indicate that the strains of the present disclosure still have the function of hydrolyzing silicon under high-salt, high-base and subacid conditions, but the control strain silicate bacterium 3016 cannot grow well under the tested adverse conditions.

TABLE 3

Strains' Ability to Hydrolyze Silicon under Different Culture Conditions

| | 1.0% Magnesium Silicate | | | | | |
|---|---|---|---|---|---|---|
| Strain | pH 6.5 | pH 10 | 5% NaCl | 10% NaCl | 5% KNO$_3$ | 10% KNO$_3$ |
| 3016 (CK) | 0 | 0 | 0 | 0 | 0 | 0 |
| MB22 | 3.5 | 2.5 | 3.5 | 1.5 | 3 | 3 |
| MB35-5 | 3 | 2 | 1 | 0.5 | 1 | 1 |
| MB35-6 | 4.5 | 2 | 1 | 0 | 3 | 2 |
| MB12-7 | 2 | 2 | 3 | 0 | 3 | 2.5 |
| MB15-13 | 3 | 2 | 2 | 0 | 3 | 2 |

6 Abilities to Survive and Hydrolyze Silicon of Strains Under Poor Oxygen Condition Results in Table 4 indicate that the activity to hydrolyze silicon of the disclosed strains MB22 and MB35-5 is significantly superior to the control silicate strain and other bacterial strains under the oxygen-deficient condition and non-oxygen-deficient condition.

TABLE 4

Abilities to Survive and Hydrolyze Silicon of Strains under Different Oxygen Concentrations

| Strain | 20% Oxygen Concentration | | 15% Oxygen Concentration | | 10% Oxygen Concentration | |
|---|---|---|---|---|---|---|
| | Growth Situation | Ability to Hydrolyze Silicon | Growth Situation | Ability to Hydrolyze Silicon | Growth Situation | Ability to Hydrolyze Silicon |
| 3016 (CK) | + | 2 | none | none | none | none |
| MB22 | + | 6 | + | 2 | + | 1.5 |
| MB35-5 | + | 5 | + | 3 | + | 1.5 |
| MB35-6 | + | 4.5 | + | 2 | + | 1 |
| MB12-7 | + | 4 | + | 2 | + | 1 |
| MB15-13 | + | 3 | + | 1.5 | + | 1.0 |

7 Hemolysis Detection

Neither of the two strains provided in the present disclosure had hemolysis loop, and experiment indicates that the disclosed strains have no hemolytic reaction.

8 Determination of Sporulation Rate: results in Table 5 indicate that under the same condition as the present experiment, the disclosed strains MB22 and MB35-5 have significantly higher sporulation rate than the control silicate strain 3016.

TABLE 5

Determination of Sporulation Rate of Strains

| Strain | 3016 (CK) | MB22 | MB35-5 |
|---|---|---|---|
| Sporulation Rate | 40% | 68% | 55% |

9 Potting Test

Results in Table 6 indicate that silicate bacterium 3016 and the disclosed strains MB22 and MB35-5 have a promoting effect on the growth of maize roots, but the promoting effect of MB22 and MB35-5 is significantly better than the silicate bacterium and the other two strains MB15-13 and MB12-7 in the experiment. Although two disclosed strains have a promoting effect on the growth of wheat roots, the effect is not as pronounced on maize. The control strain silicate bacterium 3016 has no promoting effect on the growth of wheat roots. The other two test strains also have a certain effect on the development and growth of wheat roots.

TABLE 6

Influences of Strains on Dry Weight of Roots of Different Crops

| Treatment | Maize (Zhengdan 958, gram) | Wheat (Yannong 19, gram) |
|---|---|---|
| Treated with culture solution (CK1) | 59.22 | 11.87 |
| Treated with silicate bacterium 3016 (CK2) | 65.22 | 11.48 |
| MB22 | 78.22 | 13.44 |
| MB35-5 | 81.0 | 13.35 |
| MB15-13 | 56.1 | 13.01 |
| MB12-7 | 64.7 | 12.9 |

Finally, it should be explained that the various embodiments above are merely used for illustrating the technical solutions of the present disclosure, rather than limiting the present disclosure; although the detailed description is made to the present disclosure with reference to the preceding embodiments, those ordinarily skilled in the art should understand that they still could modify the technical solutions recited in various preceding embodiments, or make equivalent substitutions to some or all of the technical features therein; and these modifications or substitutions do not make the corresponding technical solutions essentially depart from the scope of the technical solutions of the various embodiments of the present disclosure.

INDUSTRIAL APPLICABILITY

The strains in the present disclosure have the ability to hydrolyze silicon, and can also promote plant growth, and have alkali resistance, salt resistance and hypoxia resistance, thus having a very good application prospect. The strains can be used to enhance plants' health, growth or yield.

What is claimed is:

1. *Bacillus aryabhattai*, selected from:
1) an isolated *Bacillus aryabhattai* strain I, preserved in China General Microbiological Culture Collection Center, with the preservation number: CGMCC No. 17204; and preserved on Jan. 16, 2019, wherein a 16S rRNA of the isolated *Bacillus aryabhattai* strain I has the nucleotide sequence of SEQ ID NO: 1;
2) an isolated *Bacillus aryabhattai* strain II, preserved in China General Microbiological Culture Collection Center, with the preservation number: CGMCC No. 17203; and preserved on Jan. 16, 2019, wherein a 16S rRNA of the isolated *Bacillus aryabhattai* strain II has the nucleotide sequence of SEQ ID NO: 2.

2. A composition, containing a culture of the *Bacillus aryabhattai* strain according to claim 1.

3. The composition according to claim 2, wherein the composition further contains a silicon fertilizer, wherein the silicon fertilizer contains elemental silicon, an organosilicon compound and/or an inorganic silicon compound.

4. The composition according to claim 2, wherein the composition further contains a potassium fertilizer, wherein the potassium fertilizer contains elemental potassium, an organic potassium compound and/or an inorganic potassium compound.

* * * * *